United States Patent
Anderson et al.

(10) Patent No.: US 11,975,210 B2
(45) Date of Patent: May 7, 2024

(54) COMMUNICATIONS MODULE FOR USE WITH A DEFIBRILLATOR

(71) Applicant: HeartSine Technologies Limited, Belfast (GB)

(72) Inventors: Johnny Anderson, Holywood (GB); Dymphna Mary Donaghy, County Donegal (IE)

(73) Assignee: Heartsine Technologies Limited, Belfast (GB)

( * ) Notice: Subject to any disclaimer, the term of this patent is extended or adjusted under 35 U.S.C. 154(b) by 101 days.

(21) Appl. No.: 16/415,011

(22) Filed: May 17, 2019

(65) Prior Publication Data

US 2019/0351245 A1 Nov. 21, 2019

(30) Foreign Application Priority Data

May 18, 2018 (GB) .................................... 1808127

(51) Int. Cl.
*A61N 1/39* (2006.01)
(52) U.S. Cl.
CPC ......... *A61N 1/3975* (2013.01); *A61N 1/3904* (2017.08)
(58) Field of Classification Search
CPC ........................... A61N 1/3975; A61N 1/3904
See application file for complete search history.

(56) References Cited

U.S. PATENT DOCUMENTS

| | | | |
|---|---|---|---|
| 2006/0136000 A1* | 6/2006 | Bowers | A61N 1/3925 607/5 |
| 2013/0304142 A1* | 11/2013 | Curtin | H04B 7/26 361/679.41 |
| 2014/0292534 A1* | 10/2014 | Stever | H04Q 9/00 340/870.07 |

* cited by examiner

*Primary Examiner* — Gary Jackson
*Assistant Examiner* — Naveed R. Kolia

(57) ABSTRACT

A communications module adapted for use with a defibrillator, comprising a power supply system configured to supply power to the communications module, a power connector adapted for connection to the defibrillator to provide power from the communications module to the defibrillator, a power switch connected between the power supply system and the power connector to transmit power from the power supply system to the power connector, a data connector adapted for connection to the defibrillator to transfer defibrillator data between the defibrillator and the communications module, and a processor configured to control the power switch to provide power from the communications module to the defibrillator to enable the transfer of the defibrillator data between the defibrillator and the communications module.

13 Claims, 2 Drawing Sheets

COMMUNICATIONS MODULE FOR USE WITH A DEFIBRILLATOR

PRIORITY INFORMATION

The present application claims priority to United Kingdom application No. 1808127.3, filed 18 May 2018, the contents of which is incorporated herein by reference in its entirety.

BACKGROUND

1. Field of the Invention

The present disclosure related to defibrillators and more specifically to a communications module in connection with a defibrillator.

2. Introduction

Defibrillators, such as automated external defibrillators (AEDs), may be capable of wired or wireless communication with one or more networks, for example to connect to websites to obtain data from or manage the operation of the defibrillators. The communication capability is usually embedded within the defibrillator. In the use of such defibrillators with communication capability, management of the power usage of the defibrillator is critical to ensure that, in the event of a cardiac incident, the defibrillator has sufficient power.

SUMMARY

According to a first aspect of the disclosure there is provided a communications module adapted for use with a defibrillator. The communications module includes a power supply system configured to supply power to the communications module, a power connector adapted for connection to the defibrillator to provide power from the communications module to the defibrillator, a power switch connected between the power supply system and the power connector to transmit power from the power supply system to the power connector, a data connector adapted for connection to the defibrillator to transfer defibrillator data between the defibrillator and the communications module, and a processor configured to control the power switch to provide power from the communications module to the defibrillator to enable the transfer of the defibrillator data between the defibrillator and the communications module.

The processor may be configured to control the power switch to provide power from only the communications module to the defibrillator to enable the transfer of the defibrillator data between the defibrillator and the communications module. The processor may be configured to control the power switch to provide power from the communications module to the defibrillator to enable the transfer of the defibrillator data between the defibrillator and the communications module without engaging a power supply of the defibrillator. Therefore the power supply of the defibrillator is not depleted in transferring data to or from the communications module such that, in the event of a cardiac incident, the defibrillator has sufficient power to deliver a shock.

The processor may be configured to control the power switch to provide power from the communications module to the defibrillator to enable transfer of the defibrillator data from the defibrillator to the communications module.

The processor may be configured to control the power switch to provide power from the communications module to the defibrillator to enable acquisition of the defibrillator data by the defibrillator.

The processor may be configured to control the power switch to provide power from the communications module to the defibrillator to enable acquisition of the defibrillator data through a defibrillator self-test. The defibrillator self-test may be carried out daily or weekly or at any other suitable interval. The defibrillator data acquired through the defibrillator self-test may include defibrillator power supply status data. The defibrillator data acquired through the defibrillator self-test may include defibrillator electrode pack expiry data.

The processor may be configured to control the power switch to provide power from the communications module to the defibrillator to enable acquisition of cardiac incident data by the defibrillator.

The defibrillator data may include alarm data, for example, indicating tampering or vandalism of the defibrillator.

The processor may be configured to control the power switch to provide power from the communications module to the defibrillator to enable transfer of data from the communications module to the defibrillator. The data transferred to the defibrillator may include any of software updates for the defibrillator, feedback during a cardiac incident. The feedback may include real-time voice guidance.

The processor may be configured to control the power switch to provide power from the communications module to the defibrillator to enable use of the data transferred from the communications module to the defibrillator. Use of the data transferred to the defibrillator may include updating software of the defibrillator.

The processor may be configured to control the power switch by instructions embodied in software of the processor. The processor may be configured to activate the power switch to provide power from the communications module to the defibrillator.

The power connector and the data connector may be provided together in an interface unit. The interface unit may include a plurality of pin connections for the power connector. The interface unit may include a plurality of pin connections for the data connector. The interface unit may include a universal serial bus having two pin connections for the power connector and two pin connections for the data connector.

The power supply system may include a power supply. The power supply may include one or more batteries. The batteries may be rechargeable. The power supply may include mains power, which generally references the grid power, wall power or the general-purpose alternating-current electric power supply. The mains power may be supplied from a sustainable source, such as any of solar, hydro, wind, and/or wave. The power supply may include a wirelessly chargeable supply.

The power supply system may include a power supply regulator connected to the power supply. The power supply regulator may provide a first regulated power supply to the power switch. The power supply regulator may provide a second regulated power supply to the processor.

The power supply system may include a power supply status detector connected to the power supply. The power supply status detector may detect one or more power supply system characteristics and provide one or more power supply status signals to the processor. The power supply status detector may detect a level of power of the power supply and provide a power supply status signal to the processor when the detected level of power of the power supply is less than a pre-defined threshold. The power supply status detector may detect a level of power of the power supply and provide the level of power to the processor. The processor may determine if the level of power of the power supply is less than a pre-defined threshold.

The communications module may include a transmitter connected to the processor and configured to receive the defibrillator data and transmit the defibrillator data to an external system. The communications module may include a receiver connected to the processor and configured to receive data from an external system. The transmitter and receiver may be wirelessly connected to the external system.

The communications module may include a wired connector adapted for connection to an external system. The communication module may include a switch connected between the wired connector and the power and data connectors. The switch may be activated to provide power from an external system through the wired connector and the power connector to the defibrillator to enable the transfer of data to and from the defibrillator to the external circuit via the data connector and the wired connector.

The external system may include a computing device. The external system may include a network of computing devices. The external system may connect to a proprietary website enabling extraction of data from the defibrillator via the communications module. The external system may connect to a proprietary website enabling management of the defibrillator via the communications module. The external system may connect to an emergency care provider which receives cardiac incident data from and sends feedback to the defibrillator via the communications module. The external system may connect to a community response group. The external system may connect to a website which controls deployment of the defibrillator.

The communications module may include an activation switch. The communications module may include a wake-up timer which times a wake-up period and automatically activates the communications module on expiry of the wake-up period. The wake-up period may be 24 hours.

The communications module may include one or more module status indicators provided on an exterior of a housing of the module. The one or each status indicators may include a light emitting diode.

The communications module may include an audio device, such as a speaker. The audio device may be used to emit an audio alarm. The audio device may be used to convey voice feedback to a user of the defibrillator.

The communications module may include a temperature sensor configured to measure an ambient temperature around the module.

The communications module may be separate from and directly connectable to the defibrillator. The communications module may be retrofittable to the defibrillator. The communications module may be updatable as communications technology develops without having to update the defibrillator.

In providing power from the communications module to the defibrillator, the module wake ups, i.e. turns on, the defibrillator but does not activate a power supply of the defibrillator. Thus transfer, etc. of data does not use any power from the power supply of the defibrillator.

According to a second aspect of the invention there is provided a defibrillation system including one or more of a communications module according to the first aspect of the disclosure described above, and a defibrillator.

BRIEF DESCRIPTION OF THE DRAWINGS

The concepts disclosed herein will now be described by way of example only with reference to the accompanying drawings, in which.

DETAILED DESCRIPTION

Figure 1:
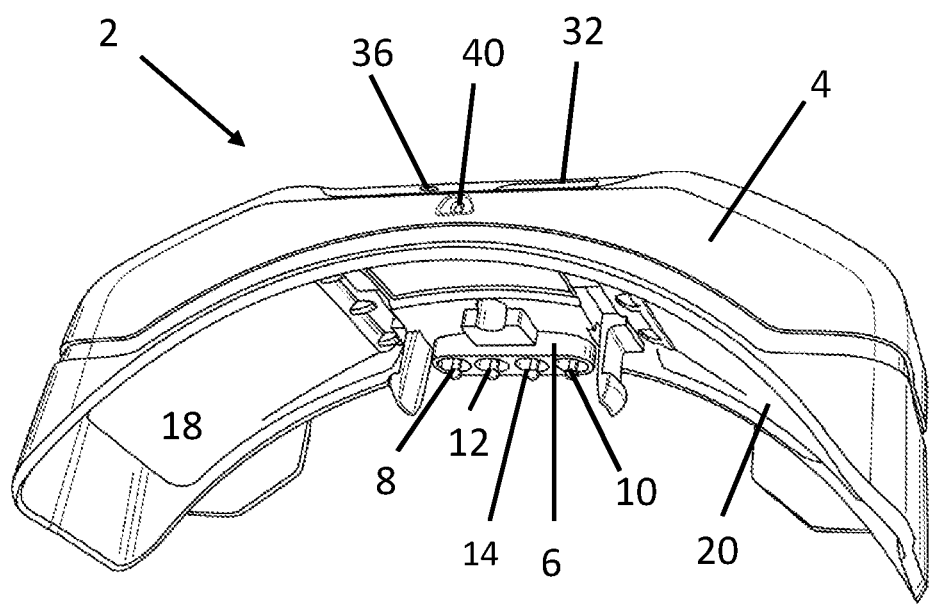
FIG. 1 is a perspective view of a communications module according to the first aspect of the invention.
Figure 2:
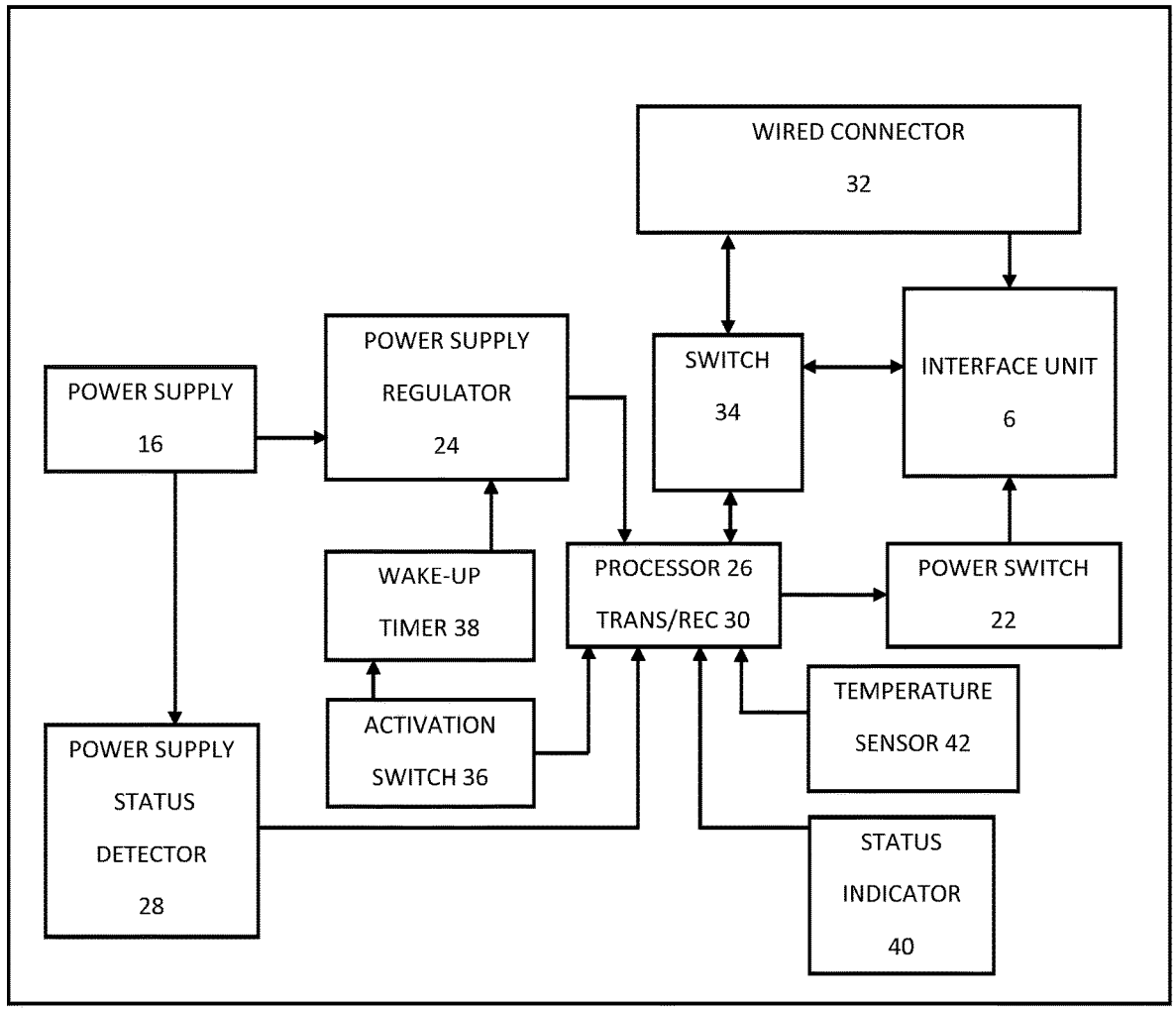
FIG. 2 is a schematic representation of internal components of the communication module of FIG. 1.

This disclosure provides various examples of defibrillators and communication modules associated with defibrillators to improvements in connection with FIG. 1 and FIG. 2.

According to a first aspect of the disclosure shown in FIG. 1, there is provided a communications module 2 adapted for use with a defibrillator. The communications module can include one or more of the following components: a power supply system configured to supply power to the communications module, a power connector adapted for connection to the defibrillator to provide power from the communications module to the defibrillator, a power switch connected between the power supply system and the power connector to transmit power from the power supply system to the power connector, a data connector adapted for connection to the defibrillator to transfer defibrillator data between the defibrillator and the communications module and/or a processor configured to control the power switch to provide power from the communications module to the defibrillator to enable the transfer of the defibrillator data between the defibrillator and the communications module.

The communications module 2 shown in FIG. 1 can be separate from and directly connectable to a defibrillator (not shown) and may be retrofittable to a defibrillator.

Referring to FIG. 1, the communications module 2 includes a housing 4 which contains components of the module shown in FIG. 2. The communications module 2 includes a power connector adapted for connection to the defibrillator and a data connector adapted for connection to the defibrillator. In this embodiment, the power connector and the data connector are provided together in an interface unit 6, which includes a universal serial bus having two pin connections 8, 10 for the power connector and two pin connections 12, 14 for the data connector.

The communications module 2 includes a power switch 22 connected to the power connector in the interface unit 6. The communications module 2 includes a processor 26 connected to the power switch 22 and configured to control the power switch 22 to provide power from the communications module 2 to the defibrillator.

The communications module 2 includes a power supply system which has a power supply 16 which, in this embodiment, includes four batteries. The housing 4 of the communications module 2 provides first and second recesses (not shown). Two batteries (or another number of batteries such as 1 or 3 or more) are placed in each recess and protected by a recess cover 18, 20.

The power supply system further includes a power supply regulator 24 connected to the power supply 16. The power supply regulator 24 provides a first regulated power supply of approximately 5V for the power switch 22 and a second regulated power supply of approximately 3V for the components of the module as required. The voltage amounts can also vary depending on the needs or application.

The power supply system further includes a power supply status detector 28 connected to the power supply 16. The power supply status detector 28 detects a level of power of the power supply 16 and provides the level of power to the processor 26. The processor 26 determines if the level of power of the power supply 16 is less than a pre-defined threshold, i.e. determines if the power level of the power supply 16 is too low.

The communications module 2 includes a transmitter/receiver 30 connected to the processor 26. In this embodiment, the transmitter/receiver 30 is provided with the processor 26 on a chip. The transmitter/receiver 30 is wirelessly connected to an external system.

The communications module 2 further includes a wired connector 32 adapted for connection to an external system including a computing device (not shown) and a switch 34 connected between the wired connector 32 and the power and data connectors in the interface unit 6. On connection of the wired connector 32 to the computing device, the switch 34 can be activated and power provided from the computing device through the wired connector 32 and the power connector of the interface unit 6 to the defibrillator. This enables the transfer of data to and from the defibrillator to the computing device of the external system via the data connector of the interface unit 6, the switch 34 and the wired connector 32.

The communications module 2 includes an activation switch 36. The communications module 2 further includes a wake-up timer 38 which times a wake-up period and automatically activates the communications module 2 on expiry of the wake-up period. The wake-up period may be 24 hours.

The communications module 2 includes a status indicator 40 provided on an exterior of the housing 4 of the module 2. The status indicator 40 includes a light emitting diode. The communications module 2 includes a temperature sensor 42 configured to measure an ambient temperature around the module 2.

In operation, the communications module 2 is attached to the defibrillator such that the power pin connections 8, 10 and the data pin connections 12, 14 of the interface unit 6 connect with corresponding connections provided on the defibrillator. The wake-up timer 38 automatically activates the communications module 2 on expiry of the wake-up period or, alternatively, the communications module 2 can be activated using the activation switch 36. The status indicator LED 40 lights up to indicate that the communications module 2 is activated. The status indicator LED 40 can also be used to indicate further status conditions, such as faults, transmitter active, and receiver active.

The power supply regulator 24 receives power from the power supply 16 and regulates this to provide a first regulated power supply of approximately 5V for the power switch 22 and a second regulated power supply of approximately 3V for the other components of the communications module 2 as required, including the processor 26. The power supply status detector 28 connected to the power supply 16, detects a level of power of the power supply 16 and provides the level of power to the processor 26. The processor 26 determines if the level of power of the power supply 16 is less than a pre-defined threshold. The processor 26 passes the level of power data to the transmitter, to transmit to an external system, such a website controlling the operation of the defibrillator. The processor 26 may also control the status indicator 40 to indicate a low power status.

The temperature sensor 42 measures the ambient temperature around the communications module 2 and sends a temperature measurement to the processor 26. This allows the storage conditions of the module 2 to be monitored.

The processor 26, connected to the power switch 22, is configured by instructions embodied in software of the processor to control the power switch 22 to provide power from the communications module 2 to the defibrillator. The processor 26 activates the power switch 22 to enable transmission of power from the power supply 16 to the power connector pin connections 8, 10 of the interface unit 6 to the defibrillator. When power from the communications module 2 is transmitted to the defibrillator, the defibrillator is enabled to acquire defibrillator data, to transfer the defibrillator data from the defibrillator to the communications module, to transfer data from the communications module to the defibrillator and to use the data transferred from the module.

In one example, when power from the communications module 2 is transmitted to the defibrillator, the defibrillator is enabled to acquire defibrillator data by carrying out a defibrillator self-test. Defibrillator data acquired through the defibrillator self-test may include defibrillator power supply status data and defibrillator electrode pack expiry data. The defibrillator data is transferred from the defibrillator to the communications module 2 via the data pin connections 12, 14 of the interface unit 6 and is passed to the processor 26. The transmitter/receiver 30 connected to the processor 26 receives the defibrillator data and wirelessly transmits the data to an external system.

In a further example, when power from the communications module 2 is transmitted to the defibrillator, the defibrillator is enabled to receive data, such as a software update, from the communications module 2 and use the data, e.g. updating software of the defibrillator. The data sent from the communications module 2 to the defibrillator is first received from an external source by the transmitter/receiver 30 and sent to the processor 26.

We claim:

1. An apparatus comprising:
  a defibrillator,
  a power supply of the defibrillator, and
  a communications module adapted for use with the defibrillator, the communications module comprising:
    a power supply system configured to supply power to the communications module,
    a power connector adapted for connection to the defibrillator to provide power from the power supply system of the communications module to the defibrillator,
    a power switch connected between the power supply system and the power connector to transmit power from the power supply system to the defibrillator via the power connector,
    a data connector adapted for connection to the defibrillator to receive electrode pack expiry data and defibrillator power supply status data, collectively defibrillator data, transmitted from the defibrillator to the communications module, and
    a processor configured to control the communications module and the power switch, as part of a defibrillator self-test, to turn on the defibrillator without activating the power supply of the defibrillator and to provide power from the communications module to the defibrillator only to enable a transfer of the defibrillator data between the defibrillator and the communications module without using any power from the power supply of the defibrillator to transfer the defibrillator data, wherein the processor is further configured to process the electrode pack expiry data and the defibrillator power supply status data.

2. The apparatus according to claim 1, in which the processor is configured to control the power switch to provide power from the communications module to the defibrillator to enable transfer of the defibrillator data from the defibrillator to the communications module.

3. The apparatus according to claim 1, in which the processor is configured to control the power switch to provide power from the communications module to the defibrillator to enable acquisition of the defibrillator data by the defibrillator.

4. The apparatus according to claim 1, in which the processor is configured to control the power switch to provide power from the communications module to the defibrillator to enable transfer of the defibrillator data from the defibrillator to the communications module.

5. The apparatus according to claim 4, in which the processor is configured to control the power switch to provide power from the communications module to the defibrillator to enable use of the defibrillator data transferred from the defibrillator to the communications module.

6. The apparatus according to claim 1, in which the power connector and the data connector are provided together in an interface unit.

7. The apparatus according to claim 1, in which the power supply system comprises any of one or more batteries, mains power, a wirelessly chargeable supply.

8. The apparatus according to claim 1, in which the power supply system comprises a power supply regulator which provides a first regulated power supply to the power switch and a second regulated power supply to the processor.

9. The apparatus according to claim 1, in which the power supply system comprises a power supply status detector which detects a level of power of the power supply system and provides the level of power to the processor which determines when the level of power of the power supply system is less than a pre-defined threshold.

10. The apparatus according to claim 1, wherein the communications module further comprises a transmitter connected to the processor and configured to receive the defibrillator data and transmit the defibrillator data to an external system.

11. The apparatus according to claim 1, wherein the communications module further comprises a receiver connected to the processor and configured to receive data from an external system.

12. The apparatus according to claim 1, in which the communications module is separate from and directly connectable to the defibrillator.

13. A defibrillation system comprising:
a defibrillator;
a power supply configured with the defibrillator; and
a communications module adapted for use with the defibrillator, the communications module comprising:
  a power supply system configured to supply power to the communications module;
  a power connector adapted for connection to the defibrillator to provide power from the power supply system of the communications module to the defibrillator;
  a power switch connected between the power supply system and the power connector to transmit power from the power supply system to the defibrillator via the power connector;
  a data connector adapted for connection to the defibrillator to receive electrode pack expiry data and defibrillator power supply status data, collectively defibrillator data, transmitted from the defibrillator to the communications module; and
  a processor configured to control the communications module and the power switch, as part of a defibrillator self-test, to turn on the defibrillator without activating the power supply of the defibrillator and to provide power from the communications module to the defibrillator only to enable a transfer of the defibrillator data between the defibrillator and the communications module without using any power from the power supply of the defibrillator to transfer the defibrillator data, wherein the processor is further configured to control the power switch to provide power from the communications module to the defibrillator to enable the defibrillator to either run the defibrillator self-test to generate the defibrillator data or to retrieve previously stored self-test defibrillator data, the processor on the communications module further configured to process the electrode pack expiry data and defibrillator power supply status data.

* * * * *